United States Patent [19]

Papenfuhs

[11] 4,429,134

[45] Jan. 31, 1984

[54] PROCESS FOR THE MANUFACTURE OF 2(3H)-BENZOTHIAZOLONES SUBSTITUTED IN 3-POSITION

[75] Inventor: Theodor Papenfuhs, Frankfurt am Main, Fed. Rep. of Germany

[73] Assignee: Hoechst Aktiengesellschaft, Fed. Rep. of Germany

[21] Appl. No.: 264,228

[22] Filed: May 18, 1981

[30] Foreign Application Priority Data

May 16, 1980 [DE] Fed. Rep. of Germany ....... 3018668

[51] Int. Cl.³ ................. C07D 277/68; C07D 277/84; C07D 497/02
[52] U.S. Cl. .................................. 548/165; 548/150; 548/175; 546/80; 546/165
[58] Field of Search ............... 548/165, 175, 176, 177, 548/150

[56] References Cited

U.S. PATENT DOCUMENTS 4,234,513 11/1980 Papenfuhs ............................. 564/26
4,252,963  2/1981 Papenfuhs ............................ 548/161
4,293,702 10/1981 Umemura et al. .................... 548/165

FOREIGN PATENT DOCUMENTS 5276 11/1979 European Pat. Off. .
2924712 12/1979 Fed. Rep. of Germany .

OTHER PUBLICATIONS

Kurzer et al., J. Chem. Soc., pp. 230–236, (1962).
*Journal of Medicinal Chemistry* 18: 315 (1975), pp. 315–318, Horgan et al., "Hypotensive Activity of 3-Alkyl-2-iminonrnxoyhisxolines".

*Primary Examiner*—Paul M. Coughlan, Jr.
*Assistant Examiner*—D. B. Springer
*Attorney, Agent, or Firm*—Connolly and Hutz

[57] ABSTRACT

A process for the manufacture of a 2(3H)-benzothiazolone compound substituted in 3-position, or of a 2(3H)-naphthothiazolone compound substituted in 3-position which comprises treating a 2(3H)-iminobenzothiazoline compound substituted in 3-position or a 2(3H)-naphthothiazoline compound substituted in 3-position with an alkali metal hydroxide or alkaline earth metal hydroxide in a solvent or diluent stable to alkalis, in the absence of water or with substantial exclusion of water, and cyclizing the alkali metal or alkaline earth metal salt of the ortho-mercapto-N-phenyl- or -naphthyl-urea compound substituted at the nitrogen atom so formed, optionally without intermediate isolation, by treatment with an acid to give the 2(3H)-benzothiazolone compound substituted in 3-position or the 2(3H)-naphthothiazolone compound substituted in 3-position. The process furnishes the final products with high yield and purity; waste water problems are excluded by this process.

4 Claims, No Drawings

PROCESS FOR THE MANUFACTURE OF 2(3H)-BENZOTHIAZOLONES SUBSTITUTED IN 3-POSITION

The invention relates to the field of intermediates and provides an improved process for the manufacture of 2(3H)-benzothiazolones substituted in 3-position.

2(3H)-Benzothiazolones substituted in 3-position which are important intermediates in industrial practice, are described for example in German Offenlegungsschrift No. 2,924,712. This Offenlegungsschrift corresponds to U.S. Pat. No. 4,293,702. The 2(3H)-benzothiazolones described in the Offenlegungsschrift are said to be effective as non-medicinal fungicides. Synthesis of this group of compounds so far has not succeeded in a satisfactory manner. The known processes are based either on industrially unavailable starting products or on those which are obtainable with great expenditure only in order to avoid ecological strain. In detail, the following methods of manufacture are known:

(a) alkylation of 2-alkylthiobenzothiazoles with subsequent hydrolysis;
(b) thermal decomposition of 3-substituted 2-nitroso-aminobenzothiazoles;
(c) reaction of N-monosubstituted o-mercaptoanilines with phosgene;
(d) alkylation of benzothiazoles;
(e) thermal rearrangement of 2-alkoxybenzothiazoles.

The processes (a) through (c) are of scientific interest only, because due to the operation mode chosen they are ecologically noxious and in part give poor yields. The process variants (d) and (e) on the other hand start from 2-chlorobenzothiazoles, for which no method of manufacture feasible on an industrial scale is known, so that they are not applicable in the technological practice.

There was thus a considerable intrest in a generally applicable, industrially feasible and improved process for the manufacture of 2(3H)-benzothiazolones substituted in 3-position.

The present invention provides now a process for the manufacture of a 2(3H)-benzothiazolone compound substituted in 3-position, or of a 2(3H)-naphthothiazolone compound substituted in 3-position which comprises treating a 2(3H)-iminobenzothiazoline compound substituted in 3-position or a 2(3H)-naphthothazoline compound substituted in 3-position with an alkali metal hydroxide or alkaline earth metal hydroxide in a solvent or diluent stable to alkalis, in the absence of water or with substantial exclusion of water, and cyclizing the alkali metal or alkaline earth metal salt of the ortho-mercapto-N-phenyl- or -naphthyl-urea compound substituted at the nitrogen atom so formed, optionally without intermediate isolation, by treatment with an acid to give the 2(3)-benzothiazolone compound substituted in 3-position or the 2(3)-naphthothiazole compound substituted in 3-position. The substituents in the 3-position are preferably alkyl, aryl and cycloalkyl radicals.

For the sake of simplicity, the starting compounds, intermediate compounds and final products used, occuring or resulting in the reaction of the invention are hereinafter called benzene derivatives, which denomination includes automatically the naphthalene derivatives.

The reaction proceeds according to the following scheme:

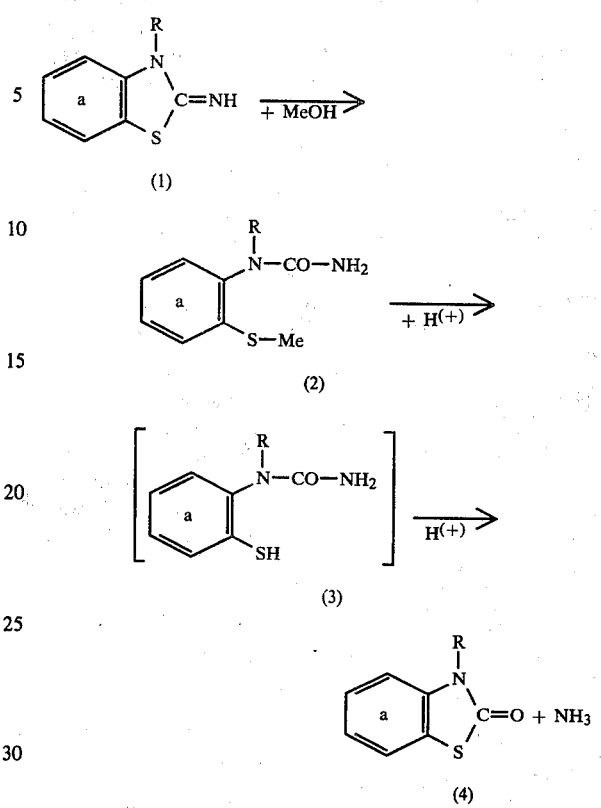

(In the formulae (1) through (4), Me is the equivalent of an alkali metal or alkaline earth metal, and the benzene nucleus a may carry further substituents; R is a substituent, preferably an optionally substituted alkyl, cycloalkyl or aryl radical, R possibly being additionally linked to the benzene nucleus a, thus forming a ring. The ammonia set free in the cyclization is bound by the acid in the form of an ammonium ion).

The alkali metal or alkaline earth metal hydroxides MeOH are preferably barium, calcium or potassium hydroxide, especially sodium hydroxide. The acids used in the reaction for cyclization of the intermediates of the formula (2) are preferably mineral acids such as hydrochloric, sulfuric or phosphoric acid.

Solvents or diluents stable to alkalis which should be anhydrous and in which the ring cleavage of the 2(3H)-benzothiazolones in 3-position, optionally also the cyclization of the mercaptophenylureas formed therefrom, is carried out, are especially aliphatic monoalcohols or polyols, for example alkanols having from 1 to 6 carbon atoms, alkaneglycols having from 2 to 5 carbon atoms, alkanetriols having from 3 to 8 carbon atoms, high molecular weight alkanepolyols and lower monoalkyl ethers of the cited glycols, triols and polyols.

It was extremely surprising to state that the 2(3H)-iminobenzothiazoline compounds substituted in 3-position easily obtainable on an industrial scale (see German Offenlegungsschrift No. 2,834,852) can be converted to 2(3H)-benzothiazolone compounds substituted in 3-position in a simple manner and with high yield and purity while using commercially available, cheap chemicals not raising any waste water problems. For, it is known from Chem. Ber. 13, 20 (1880) that on treatment with molten alkali, the related species of 2-aminobenzothiazoles are irreversibly split into o-aminothiophenolates and ammonia and alkali metal carbonates, the heterocycle being destroyed in this reaction. In contrast thereto, a gentle ring opening is ensured in accordance with the present invention, in which process practically no ammonia escapes, and the alkali metal salts or alkaline earth metal salts of the corresponding o-mercaptophenylureas (see formula (2) above) are obtained as intermediates with high, often nearly quantitative, yields. These stable mercaptides of the formula (2) can subsequently be converted, either directly of after intermediate isolation, to the 2(3H)-benzothiazolones substituted in 3-position by treatment with acid.

This acid-catalytic cyclization of the compounds of the formulae (2) and (3), respectively, to form the 2(3H)-benzothiazolone substituted in 3-position of the formula (4), although known as analogous reaction from J.Chem.Soc. 1962, 230, has not been realized hitherto on an industrial scale in adaptation to the above compounds of the formula (2) or (3), because preparation of the starting compounds of the formula (3) was possible only by reaction of ortho-aminothiophenols with excess sodium cyanate, in which reaction the cited ecological and synthesis problems were involved.

By finding the new process for the preparation of the key compounds of the formulae (2) and (3), resplectively, 2(3H)-benzothiazolone compounds substituted in 3-position can be manufactured now in a simple and technically advantageous manner from easily obtainable precursors.

Suitable 2(3H)-iminobenzothiazoline compounds serving as starting compounds according to the invention are preferably those which are described in German Offenlegungsschrift No. 2,834,852. Especially preferred according to the process of the invention is the manufacture of a benzothiazolone of the formula (4a)

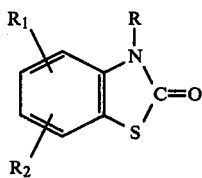

in which $R_1$ and $R_2$ are identical or different and each is a hydrogen atom, an alkyl group, referably a lower alkyl group, an alkoxy group, preferably a lower alkoxy group, a halogen atom, preferably fluorine or chlorine, a hydroxy, nitro or sulfo group, or $R_1$ and $R_2$ together with the nucleus a are a naphthalene nucleus, and R is an alkyl radical which can be substituted, or is a cycloalkyl or aralkyl or aryl radical, this radical possibly being linked with the benzene nucleus a in o-position. Preferably, R is an alkyl radical having from 1 to 5 carbon atoms which can carry one or two substituents selected from the group of vinyl, phenyl, phenyl substituted by substituents selected from the group of methyl, ethyl, methoxy, ethoxy and chlorine, amino, dimethylamino, diethylamino, hydroxy, lower alkoxy and piperidino, or R is preferably a cyclohexyl radical or a phenyl radical which can carry substituents selected from the group of methyl, ethyl, hydroxy, methoxy, ethoxy and chlorine, or R is preferably a propylene radical forming with the benzene nucleus a in o-position and the nitrogen a heterocyclic ring, while starting according to the invention from a 2-iminobenzothiazoline of the formula (1a)

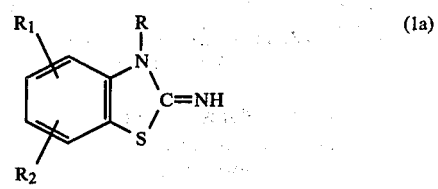

in which R, $R_1$ and $R_2$ are as defined above.

The process according to the invention of ring cleavage of the 2(3H)-iminobenzothiazolines substituted in 3-position to yield the o-mercaptophenylureas substituted at the nitrogen atom, for example of formula (2), must be carried out in an anhydrous or practically anhydrous medium in order to ensure high yields. Although small amounts of water contained in the solvents or diluents may be present, the yield and possibly the purity of the products, however, is decreased in this case. It is therefore required in accordance with the invention to carry out the ring cleavage of the 2(3H)-iminobenzothiazolines substituted in 3-position with substantial exclusion of water, that is, advantageously in the presence of 2.5 weight % at most, preferably 0.5 weight % at most, of water in the reaction mixture and relative thereto.

The reaction temperature of the process step according to the invention for obtaining the compounds of the formula (2) is in a range of from 80° to 200° C.; preferably from 120° to 160° C. When low-boiling solvents or diluents are used, such as alkanols having 1 to 3 carbon atoms, or lower glycolmonoalkyl ethers, the reaction should be carried out in a closed system and under pressure.

The alkali metal or alkaline earth metal hydroxide is used for the ring cleavage reaction in an at least stoichiometric amount. In order to prevent side reactions, an excess of an 1- to 4-fold, preferably 2- or 3-fold, molar amount of alkali metal or alkaline earth metal hydroxide has proved to be favorable.

The alkali metal or alkaline earth metal salts of ortho-mercaptophenylureas prepared according to the invention are subsequently converted with acid to the ortho-thiophenolurea compounds, optionally after separation from the reaction medium by removal of the solvent or diluent. Equivalent amounts of acid are required for this step. The subsequent cyclization of these thiophenolureas to yield the 2(3H)-benzothiazolones substituted in 3-position can be carried out with catalytic or excess amounts of acid, in a solvent or diluent, preferably, however, in the aqueous medium of the acid applied. The temperature of this cyclization reaction is in a range of from 40° to 100° C., preferably 60° to 90° C. The reaction is complete within a short period of time.

The process of the invention may be carried out as follows: a 2(3H)-iminobenzothiazoline compound substituted in 3-position, for example of the formula (1) or (1a), is heated, while stirring, in an anhydrous or practically anhydrous solvent, for example ethanol, isobutanol, 1,2-dihydroxypropane or 1,3-dihydroxypropane, preferably ethyleneglycol, glycerol, ethyleneglycol-monomethyl ether or ethyleneglycol-monoethyl ether, together with the solid alkali metal or alkaline earth metal hydroxide, preferably sodium hydroxide, to a temperature of from 120° to 160° C., and the reaction is allowed to proceed for several hours within this temperature range. The complete conversion can be stated by chromtographic analysis for starting material. Practically no ammonia escapes in this ring opening reaction. The alkali metal or alkaline earth metal salt of the N-substituted o-mercaptophenylurea compound formed precipitates in crystallized form from the reaction mixture; it can be separated by filtration from the optionally recyclizable mother liquor and subjected to the cyclization reaction. On the other hand, the salt of the N-substituted o-mercaptophenylurea compound formed can be left in the reaction medium and directly converted to the free N-substituted o-mercaptophenylurea compound by adding an at least stoichiometric amount of mineral acid, relative to alkali metal or alkaline earth metal hydroxide used, which free compound can be isolated by filtration, for example after addition of water. However, due to the instability of these free N-substituted o-mercaptophenylurea compounds, it is recommended to cyclize them or their salts directly in the acidic medium by a short-time heating in order to form the intended 2(3H)-benzothiazolone compound substituted in 3-position. In this latter case, the final product is isolated either by filtration from the solvent used, optionally after further dilution with water, or by blowing off the solvent and subsequently mechanically separating the suspension obtained, for example by means of filter press, separator or centrifuge. When starting from the isolated salt of the N-substituted o-mercaptophenylurea compound or the isolated free mercapto compound for the cyclization, these compounds are dissolved or suspended in water which may contain a further solvent or diluent; after addition of acid until an acidic pH has adjusted, this mixture is heated to 40°–100° C., preferably 60° to 90° C.

In some cases, the operations may alternatively be as follows: After the ring cleavage, the solvent or diluent is distilled off from the alkaline reaction mixture or blown off by means of steam, and acid, preferably aqueous acid, is added to the salt of o-mercaptophenylurea compound or the aqueous solution thereof until the pH has adjusted in the acidic range, and the batch is then heated in the above temperature range.

The process of the invention starts from compounds easily obtainable on an industrial scale, and furnishes the corresponding 2(3H)-benzothiazolone compounds substituted in 3-position with high yield and quality, in technologically simple operation steps and in an ecologically favorable manner.

The following examples illustrate the invention; parts and percentages being by weight unless otherwise stated. The relation of parts by weight to parts by volume is that of kilogram to liter.

EXAMPLE 1

A mixture of 164 parts of 2-iminobenzothiazoline, 150 parts of sodium hydroxide and 300 parts of ethyleneglycol is stirred for 6 hours at 130°–140° C., subsequently cooled to 80° C., and introduced with agitation into 3000 parts of icewater. After further agitation for 30 minutes, 5 parts of active charcoal are added, the solution is stirred for a further 15 minutes and then filtered. The pH of the filtrate is adjusted to 5–6 by means of 10% aqueous hydrochloric acid, and the precipitated N-methyl-N-(2-mercaptophenyl)-urea is isolated by filtration. The moist product is immediately introduced into 700 parts of a 10% aqueous hydrochloric acid and heated for 15 minutes with agitation at 90° C. The precipitating 3-methyl-2(3H)-benzothiazolone of the formula

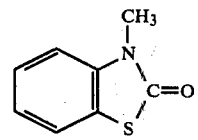

is isolated by filtration after cooling the acidic batch, washed with water and dried. 150 Parts of an analytically pure product are obtained; this corresponds to a yield of 90.9% of theory, relative to 2-iminobenzothiazoline, melting point 73°–75° C.

When instead of sodium hydroxide, equivalent parts of potassium hydroxide or barium hydroxyde are used and operations are as indicated above, 3-methyl-2(3H)-benzothiazolone is obtained with an about similar yield and quality.

EXAMPLE 2

A mixture of 138 parts of 3-phenyl-6,7-benzo-2(3H)benzothiazoline, 50 parts of sodium hydroxide and 150 parts of glycerol is stirred for 12 hours at 150° C., and subsequently slowly introduced into 2000 parts of icewater. The solution of sodium salt of N-phenyl-N-(1-mercapto-naphth-2-yl)-urea of the formula

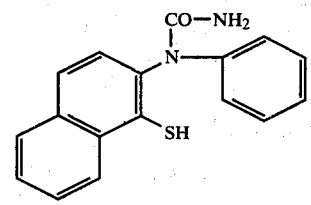

so obtained is clarified after addition of 2.5 parts of active charcoal. 250 Parts of a 30% aqueous hydrochloric acid are added to the filtrate, and the batch is heated for 15 minutes with agitation at 85°–90° C., and the whole is then cooled to 20° C. The precipitated 3-phenyl-6,7-benzo-2(3H)-benzothiazolone of the formula

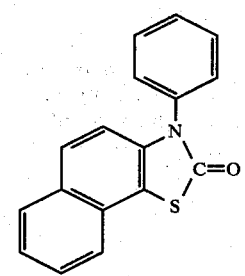

is isolated by filtration, washed with water and dried. 130.9 Parts of an analytically pure product having a melting point of 143°–145° C. are obtained, which corresponds to a yield of 94.5% of theory.

Operations are as described above, however, the hydrochloric acid added to the filtrate containing the mercaptonaphthyl urea is replaced by an equivalent amount of sulfuric or phosphoric acid. A product of identical purity and yield is obtained.

Operations are as described above; however, instead of glycerol as solvent there is used an identical amount of 1,2-dihydroxypropane or 1,3-dihydroxypropane. The naphthothiazolone is obtained with similar yield and quality.

EXAMPLE 3

A mixture of 106.25 parts of 3-ethyl-6-chloro-2-iminobenzothiazoline, 60 parts of sodium hydroxide and 150 parts of isobutanol is stirred for 9 hours at 140° C. in an autoclave. After cooling, the suspension of sodium salt of N-ethyl-N-(4-chloro-2-mercapto-phenyl)-urea obtained is filtered off, the filter residue is washed with isobutanol and dried under reduced pressure. 116.4 Parts of the sodium salt of this thio compound are obtained, corresponding to a yield of 92.2% of theory. It is introduced into 400 parts of a 10% aqueous hydrochloric acid and the suspension obtained is heated for 30 minutes at 80° C., thus causing first solution of the product and subsequently precipiatation of the colorless 3-ethyl-6-chloro-2(3H)benzothiazolone which is filtered after cooling, washed with water and dried. 95.5 Parts, corresponding to a yield of 89.5% of th., of a practically analytically pure product having a melting point of 112°-114° C. are obtained.

EXAMPLE 4

When the operation mode of Example 3 is varied in that the isolated sodium salt of the mercaptophenylurea is left in moist state containing the isobutanol, and is introduced, without being dried, into the cited amount of hydrochloric acid, and this suspension is heated for 30 minutes at 80° C., cooled, filtered, washed with water and dried, 97 parts of 3-ethyl-6-chloro-2(3H)benzothiazolone (corresponding to a yield of 90.0% of th.) having a melting point of 111°-113° C., are obtained.

EXAMPLE 5

Operations are as indicated in Example 3 or 4; however, the solvent isobutanol is replaced by an identical amount of n-butanol or ethanol or ethyleneglycolmonomethyl ether. These process variant gives 3-ethyl-6-chloro-2(3H)benzothiazolone with an about identical purity and yield.

EXAMPLE 6

A mixture of 95.0 parts of 3,4-trimethylene-2-iminobenzothiazoline, 100 parts of ethyleneglycol and 60 parts of sodium hydroxide is heated for 4 hours with agitation at 160° to 165° C. Subsequently, the batch is cooled with agitation to a temperature of 20°-30° C., and the precipitated sodium salt of 8-mercapto-1,2,3,4-tetrahydroquinoline-N-carbonamide of the formula

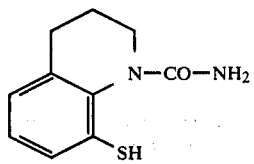

is isolated by suction-filtration and washed with 20 parts of ethyleneglycol. The glycolic filtrate can be reused for the next batch for hydrolytic ring opening of 3,4-trimethylene-2-iminobenzothiazoline.

The moist filter residue containing the glycol is introduced in 300 parts of a 10% aqueous hydrochloric acid. This mixture is then heated for 60 minutes with agitation at 80°-85° C. After cooling, the precipitated 3,4-trimethylene-2(3H)benzothiazolone of the formula

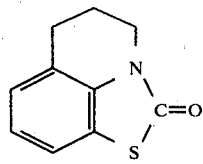

is isolated by filtration, the residue is washed with water to neutral and dried. 62.8 Parts (corresponding to a yield of 65.8% of th.) of a nearly pure product having a melting point of 76°-77° C. are obtained; it distills at 184° C./4 mbar constantly. The distillate has a melting point of 77.5°-78° C. and is analytically pure.

When the glycolic reaction mixture is worked up according to Example 1, the 3,4-trimethylene-2(3H)benzothiazolone is obtained in corresponding purity with a yield of 89.8% of th.

EXAMPLE 7

95.0 Parts of 3,4-trimethylene-2-iminobenzothiazoline, and 20 parts only of sodium hydroxide are added to the glycolic mother liquor of Example 6 and the batch prepared is heated for 4 hours at 160°-165° C. under stirring. It is then cooled with further agitation to a temperature of 20°-30° C., and operations for cyclization and work-up are as indicated in Example 6. 86 Parts of 3,4-trimethylene-2(3H)-benzothiazolone having a melting point of 77.5°-78° C. are obtained, which corresponds to a yield of 90.1% of th.

EXAMPLE 8

Operations are as indicated in Example 6 and subsequently as in Example 7; however, the starting compound is replaced by the equivalent amount of 3,4-dimethyl-2-iminobenzothiazoline. Via the intermediate stage of the sodium salt of N-methyl-N-6-methyl-2-mercaptophenylurea the 3,4-dimethyl-2(3H)benzothiazolone is obtained as final product with a yield of 69.3% of theory according to the operation mode of Example 6 and of 94.0% of theory according to the operation mode of Example 7; the melting point being 123° to 125° C. in each case.

EXAMPLES 9 TO 42

When preparing a 2(3H)benzothiazolone compounds substituted in 3-position according to the invention, for example analogously to a method as described in one of the above Examples, while using as the starting compound a compound of the formula (1a) the radicals R, $R_1$ and $R_2$ as indicated in the Examples of the following Table, the corresponding compound of the formula (4a) having the corresponding substitutents R, $R_1$ and $R_2$ also as indicated in the Table is obtained with the yield and melting and/or boiling points as further indicated in the Table.

| | Compound (1a) or (4a) | | | Yield | m.p. | b.p. |
|---|---|---|---|---|---|---|
| Ex. | R | $R_1$ | $R_2$ | (% of th.) | (°C.) | (°C./mbar) |
| 9. | cyclohexyl | H | H | 85.3 | 72 | |

-continued

| | Compound (1a) or (4a) | | | Yield | m.p. | b.p. |
|---|---|---|---|---|---|---|
| Ex. | R | $R_1$ | $R_2$ | (% of th.) | (°C.) | (°C./mbar) |
| 10 | benzyl | H | H | 90.0 | 88 | 178/2.7 |
| 11 | —$(CH_2)_2$—$N(C_2H_5)_2$ | H | H | 81.9 | | 158/2.7 |
| 12 | β-(piperidin-1-yl)ethyl | H | H | 82.2 | | 171/1.3 |
| 13 | —$(CH_2)_3$—$N(C_2H_5)_2$ | H | H | 80.7 | | 152/4.0 |
| 14 | phenyl | H | H | 92.2 | 82 | 227/21 |
| 15 | methyl | 6-$CH_3$ | H | 91.5 | 77 | |
| 16 | ethyl | 6-$CH_3$ | H | 84.0 | 58 | 132/1.3 |
| 17 | o-methylphenyl | 4-$CH_3$ | H | 94.6 | 116 | 211/9.3 |
| 18 | p-methylphenyl | 6-$CH_3$ | H | 93.0 | 106 | |
| 19 | methyl | 5-$OCH_3$ | H | 84.2 | 107 | |
| 20 | methyl | 6-$OC_2H_5$ | H | 90.8 | 85 | |
| 21 | methyl | 4-F | H | 92.8 | 124 | |
| 22 | methyl | 4-Cl | H | 96.1 | 132 | |
| 23 | ethyl | 4-Cl | H | 88.7 | 99 | |
| 24 | n-propyl | 4-Cl | H | 85.0 | 48 | 110/0.25 |
| 25 | n-pentyl | 4-Cl | H | 83.0 | | 129/0.25 |
| 26 | methyl | 5-Cl | H | 89.3 | 105 | |
| 27 | methyl | 6-Cl | H | 93.0 | 112 | |
| 28 | benzyl | 6-Cl | H | 97.1 | 145 | |
| 29 | methyl | 4-Br | H | 96.5 | 138 | |
| 30 | methyl | 6-$NO_2$ | H | 89.0 | 162 | |
| 31 | methyl | 4-$CH_3$ | 6-$CH_3$ | 91.4 | 151 | |
| 32 | methyl | 4-$CH_3$ | 6-Cl | 92.7 | 131 | |
| 33 | methyl | 4-$CH_3$ | 7-Cl | 87.0 | 129 | |
| 34 | ethyl | H | H | 91.2 | | 152/5.7 |
| 35 | n-propyl | H | H | 87.2 | | 130/1.3 |
| 36 | n-butyl | H | H | 82.8 | | 150/4 |
| 37 | i-amyl | H | H | 80.2 | | 144/4 |
| 38 | ethyl | 6,7-benzo | | 81.9 | 135 | 200/6.7 |
| 39 | o-methylphenyl | 6,7-benzo | | 96.0 | 118 | |
| 40 | p-methylphenyl | 6,7-benzo | | 94.8 | 171 | |
| 41 | p-hydroxyphenyl | 6,7-benzo | | 90.1 | 215 | |
| 42 | p-methoxyphenyl | 6,7-benzo | | 87.4 | 159 | |

What is claimed is:

1. A process for the manufacture of a 2-benzothiazolone compound of formula

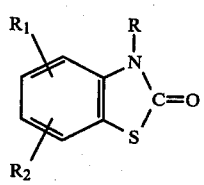

in which
$R_1$ and $R_2$ are identical or different and each is hydrogen, alkyl, or halogen, and R is unsubstituted alkyl having from 1 to 5 carbon atoms,
which comprises reacting, at a temperature within the range of 80°–200° C., a 2-imino-benzothiazoline compound of formula

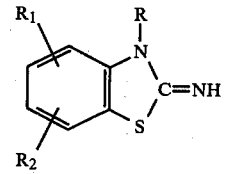

in which R, $R_1$ and $R_2$ are as defined above, with an alkali metal hydroxide or alkaline earth metal hydroxide in a substantially anhydrous solvent or diluent medium stable to alkalis, said substantially anhydrous medium containing less than about 2.5% by weight of water, and the cyclizing the alkali metal or alkaline earth metal salt of the ortho-mercapto-N-phenyl urea compound so formed by reaction with an acid at a temperature of from 40° to 100° C.

2. A process according to claim 1 wherein the reacting with the alkali metal hydroxide or alkaline earth metal hydroxide is carried out at a temperature of from 120° to 160°.

3. A process according to claim 1 wherein the cyclizing is carried out without isolation of the alkali metal or alkaline earth metal salt of the ortho-mercapto-N-phenyl-urea compound.

4. A process according to claim 1 wherein the reacting with an alkali metal hydroxide or alkaline earth metal hydroxide is carried out in the absence of water.

* * * * *

UNITED STATES PATENT AND TRADEMARK OFFICE
CERTIFICATE OF CORRECTION

PATENT NO. : 4,429,134
DATED : January 31, 1984
INVENTOR(S) : THEODOR PAPENFUHS

It is certified that error appears in the above-identified patent and that said Letters Patent is hereby corrected as shown below:

In claim 1, column 10, line 47, the word "the" prior to "cyclizing" should read -- then --.

Signed and Sealed this

Ninth Day of October 1984

[SEAL]

Attest:

GERALD J. MOSSINGHOFF

Attesting Officer

Commissioner of Patents and Trademarks